(12) United States Patent
Lee et al.

(10) Patent No.: US 10,895,446 B2
(45) Date of Patent: Jan. 19, 2021

(54) SENSOR-INTEGRATED DISPOSABLE COVER

(71) Applicant: Microsoft Technology Licensing, LLC, Redmond, WA (US)

(72) Inventors: Woo Suk Lee, Redmond, WA (US); Sang Ho Yoon, Redmond, WA (US); Flavio Protasio Ribeiro, Bellevue, WA (US); James David Holbery, Bellevue, WA (US); Siyuan Ma, Bothell, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 217 days.

(21) Appl. No.: 16/124,031

(22) Filed: Sep. 6, 2018

(65) Prior Publication Data

US 2020/0080832 A1 Mar. 12, 2020

(51) Int. Cl.
| | |
|---|---|
| *G01B 7/30* | (2006.01) |
| *A41D 1/00* | (2018.01) |
| *A41D 19/00* | (2006.01) |
| *G01N 27/12* | (2006.01) |

(52) U.S. Cl.
CPC ............. *G01B 7/30* (2013.01); *A41D 1/002* (2013.01); *A41D 19/0027* (2013.01); *G01N 27/12* (2013.01); *G01B 2210/58* (2013.01)

(58) Field of Classification Search
CPC .... A41D 19/0027; A41D 1/002; A61B 42/10; A61B 5/01; A61B 5/1114; A61B 5/14532; A61B 5/14546; A61B 5/6806; G01B 2210/58; G01B 7/30; G01N 27/02; G01N 27/12; G01N 27/223; G01N 27/3271; G01N 33/0036; G01N 33/0047; G06F 3/014; G06F 3/017
See application file for complete search history.

(56) References Cited

U.S. PATENT DOCUMENTS

| | | | | |
|---|---|---|---|---|
| 9,189,022 | B2 * | 11/2015 | Burgess | ............. G06F 3/014 |
| 9,779,352 | B1 * | 10/2017 | Hyde | ............. G06K 19/041 |
| 2009/0053104 | A1 | 2/2009 | Buttner et al. | |
| 2014/0129174 | A1 | 5/2014 | White et al. | |
| 2014/0215684 | A1 | 8/2014 | Hardy et al. | |
| 2016/0048205 | A1 | 2/2016 | Baier et al. | |

(Continued)

OTHER PUBLICATIONS

Lee, et al., "TeleProbe: Zero-power Contactless Probing for Implantable Medical Devices", In Proceedings of the International Symposium on Low Power Electronics and Design, Aug. 8, 2016, 6 Pages.

(Continued)

*Primary Examiner* — Francis C Gray
(74) *Attorney, Agent, or Firm* — Alleman Hall Creasman & Tuttle LLP (57) ABSTRACT

Examples are disclosed that relate to a disposable cover for an object, wherein the cover includes a passive sensing circuit loop. The sensing circuit loop is configured to inductively couple with a reusable sensor readout device that provides power and signal processing. The reusable sensor readout device wirelessly measures a sensor element printed as part of the sensing circuit loop through the inductively coupled channel. In one example, a disposable glove for a human hand includes a sensing circuit loop printed on the disposable glove.

19 Claims, 6 Drawing Sheets

(56) References Cited

U.S. PATENT DOCUMENTS

| | | | |
|---|---|---|---|
| 2016/0187973 A1* | 6/2016 | Shankar | G09G 5/18 345/156 |
| 2017/0094727 A1 | 3/2017 | Saunamaki | |
| 2017/0176267 A1* | 6/2017 | Keller | G01L 1/146 |
| 2018/0190106 A1 | 7/2018 | Hamain et al. | |
| 2019/0050052 A1* | 2/2019 | Hogbin | G06F 3/014 |
| 2019/0101981 A1* | 4/2019 | Elias | D04B 21/207 |
| 2019/0311648 A1* | 10/2019 | Alshami | A41D 19/0027 |

OTHER PUBLICATIONS

Mishra, et al., "Wearable Flexible and Stretchable Glove Biosensor for On-Site Detection of Organophosphorus chemical Threats", In Journal of ACS Sensors, vol. 2, Issue 4, Mar. 3, 2017, 9 Pages.

Shen, et al., "A soft stretchable bending sensor and data glove applications", In Journal of Robotics and Biomimetics, vol. 3, Issue 1, Dec. 1, 2016, pp. 1-8.

Tongrod, et al., "A Low-Cost Data-Glove for Human Computer Interaction Based on Ink-Jet Printed Sensors and ZigBee Networks", In Proceedings of International Symposium on Wearable Computers, Oct. 2010, 3 Pages.

Watthanawisuth, et al., "Design and development of data glove based on printed polymeric sensors and Zigbee networks for Human-Computer Interface", In Journal of Disability and Rehabilitation: Assistive Technology, vol. 8, Issue 2, Mar. 1, 2013, pp. 115-120.

"Application as Filed in U.S. Appl. No. 16/044,258", filed Jul. 24, 2018, 40 Pages.

"Application as Filed in U.S. Appl. No. 16/046,708", filed Jul. 26, 2018, 45 Pages.

"International Search Report and Written Opinion Issued in PCT Application No. PCT/US2019/038850", dated Nov. 11, 2019, 17 Pages.

* cited by examiner

SENSOR-INTEGRATED DISPOSABLE COVER

BACKGROUND

A sensing device for measuring a physical quantity may include a sensing circuit as well as electrical power components and signal processing components that collectively enable sensing functionality. In some instances, all of these components may be integrated into a reusable glove to provide the reusable glove with sensing functionality.

SUMMARY

Examples are disclosed that relate to a disposable cover for an object, wherein the cover includes a passive sensing circuit loop. The sensing circuit loop is configured to inductively couple with a reusable sensor readout device that provides power and signal processing. The reusable sensor readout device wirelessly measures a sensor element printed as part of the sensing circuit loop through the inductively coupled channel. In one example, a disposable glove for a human hand includes a sensing circuit loop printed on the disposable glove.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

A sensing device including a sensing circuit, electrical power components, and signal processing components may be integrated into a reusable glove to provide the glove with sensing functionality. However, throughout the course of using the reusable glove, the material that makes up a body of the reusable glove (e.g., fabric) may degrade faster than the electrical components of the integrated sensing device. In such an example, due to the reuseable all-in-one implementation, the body of the glove cannot be replaced without also having to replace the integrated sensing device, which may be prohibitively expensive depending upon a frequency of replacement. Additionally, such a reusable glove may be unsuitable for use in highly sanitary applications, as it may be non-sanitizable.

Accordingly, examples are disclosed that relate to a disposable, low-cost, sensing-enabled glove including a passive sensing circuit loop that is printed on the disposable glove. The passive sensing circuit loop includes a sensor element located on one portion of the disposable glove, and an inductive coil located on a different portion of the disposable glove. The disposable glove does not include any active electrical components. Instead, electrical power and signal processing components for sensing measurement are located on a reusable sensor readout device. The reusable sensor readout device may be configured to wirelessly measure electrical behavior of the sensor element through an inductive channel. The reusable sensor readout device may form the inductive channel by driving an inductive coil of the reusable sensor readout device with an electrical current to inductively couple the inductive coil of the readout device with the inductive coil of the sensing circuit loop printed on the disposable glove. As the active electrical components are offloaded from the disposable glove, the disposable glove can be replaced at low cost.

Figure 1:
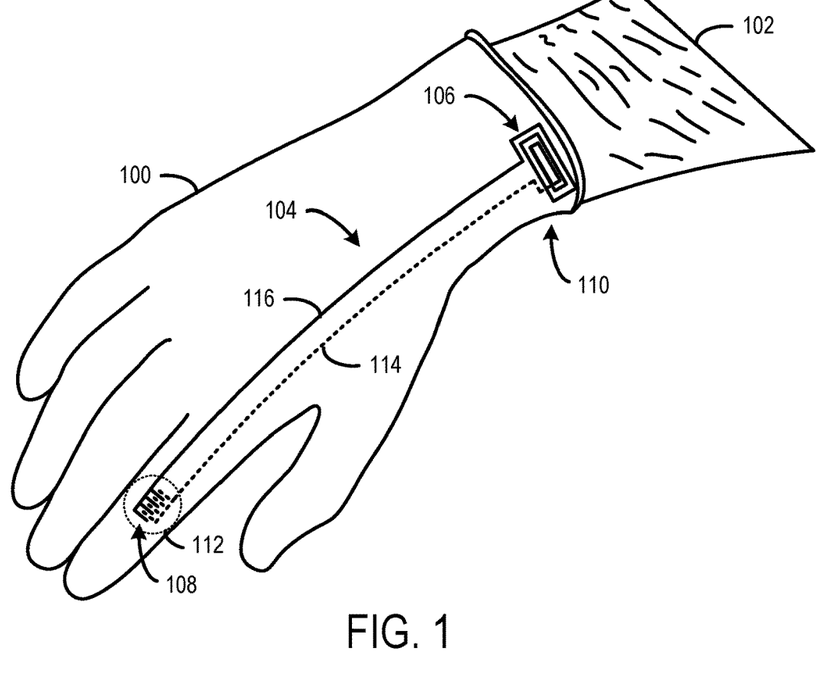
FIG. 1 schematically shows an example disposable glove comprising a sensing circuit loop including a capacitive sensor element.

FIG. 1 shows an example sensing-enabled, disposable glove 100 for a human hand 102. The disposable glove 100 may comprise any suitable thin and flexible material that responds quickly and accurately to movement of the human hand 102. For example, the disposable glove may comprise a flexible polymer (e.g., rubber latex), a flexible fabric (e.g., cotton, lycra, nylon, spandex), or another flexible material. A sensing circuit loop 104 is printed on the disposable glove 100. The depicted sensing circuit loop 104 includes an inductive coil 106 and a capacitive sensor element 108, but may include any other suitable components in other examples. The inductive coil 106 is printed on a wrist portion 110 of the disposable glove 100, and the capacitive sensor element 108 is printed on a bendable finger joint portion 112 of the disposable glove 100. The pattern of the sensing circuit loop 104 forms a passive inductor-capacitor (LC) tank circuit, where the capacitive sensor element 108 functions as a sensor for measuring a physical quantity. In other words, the capacitive sensor element 108 converts the physical quantity (e.g., angle of joint) into a capacitance that can be measured.

The inductive coil 106 may allow a reusable sensor readout device (shown in FIGS. 6 and 7) to inductively couple with the sensing circuit loop 104. When inductively coupled, the reusable sensor readout device may perform a frequency scan of the sensing circuit loop to measure the capacitance of the capacitive sensor element 108 based on the electrical behavior, and converts the measured capacitance into a corresponding physical quantity. In one example, the reusable sensor readout device measures the physical quantity by determining a resonant frequency that monotonically varies according to changes in capacitance.

Figure 2:
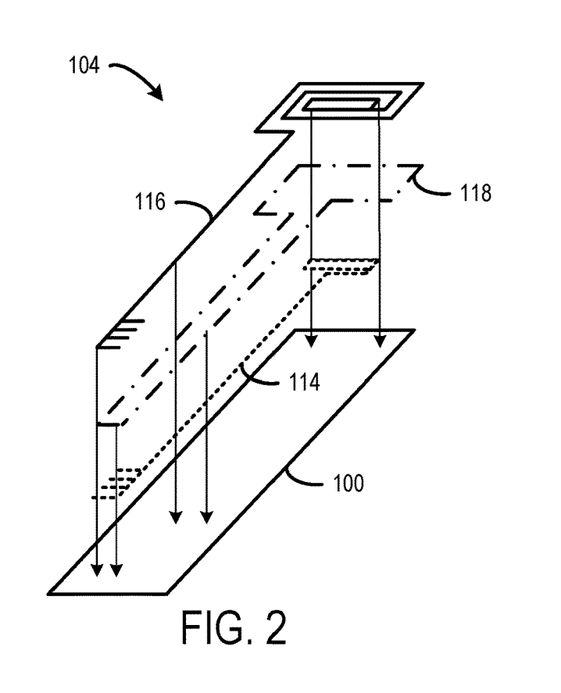
FIG. 2 schematically shows layers of an example sensing circuit loop that allow via-less construction.

As shown in FIG. 2, the sensing circuit loop 104 comprises a plurality of separate layers of conductive material. In some examples, the conductive material can be directly printed on the disposable glove 100. In other examples, the conductive material can be printed on a separate substrate that can be attached onto the disposable glove 100. The layers of conductive material 114, 116 may comprise any suitable material having conductivity. In one example, the sensing circuit loop 104 comprises layers of silver ink. The adjacent layers of conductive material 114, 116 are electrically insulated by a dielectric layer 118. In one example, the dielectric layer 118 comprises a curable resin, such as an ultraviolet radiation-curable resin. In another example, the dielectric layer 118 comprises a laminated film, such as a polypropylene or polycarbonate film. In some examples, the material used in the dielectric layer also may be used to bond the layers of conductive material of the sensing circuit loop 104 to the disposable glove 100.

In the illustrated example, capacitive plates printed on adjacent layers of conductive material may create a capacitor at the center of the inductive coil that allows the sensing circuit loop to be electrically closed without the use of a mechanical via. By connecting the different conductive layers through the capacitive plates, the manufacturing process for the sensing circuit loop may be simplified relative to a sensing circuit loop having different conductive layers that are connected by a mechanical via. However, in some examples, the sensing circuit loop may use a via to mechanically provide a conduction path between layers of conductive material that are electrically insulated by a dielectric layer.

The capacitive sensor element 108 connected in series with the inductive coil 106 forms a closed sensing circuit loop 104 such that both layers can receive electrical power during a frequency scan performed by the reusable sensor readout circuit. In the depicted example, the sensing circuit loop 104 comprises two layers of conductive material. In other examples, the sensing circuit loop may comprise a different number of layers of conductive material (e.g., more than two layers).

The sensing circuit loop 104 may be printed on or otherwise affixed to the disposable glove 100 using any suitable printing process. In one example, sensing circuit loop 104 is printed on the disposable glove 100 using a screen-printing process. The material used to form the sensing circuit loop 104 and the printing process may depend on the material of the disposable glove 100. In other examples, the sensing circuit loop may be printed using an inkjet process, a gravure process, screen printing, aerosol jet printing, etc.

The sensing circuit loop 104 may be printed on any suitable surface of the disposable glove 100. In some examples, the sensing circuit loop 104 may be printed on an exterior surface of the disposable glove 100. In other examples, the sensing circuit loop 104 may be printed on an interior surface of the disposable glove 100. In yet other examples, the sensing circuit loop 104 may be printed in between different layers of material of the disposable glove 100.

In the depicted example, the capacitive sensor element 108 is positioned on a bendable finger joint portion 112 of the disposable glove 100 to align with an upper finger joint of the index finger when the disposable glove 100 is worn on the human hand 102. The capacitive sensor element 108 is configured as a motion sensor that measures a change in posture/position/angle of the finger joint. For example, such finger motion tracking may be employed in a mixed-reality application, such as a visually enhanced medical procedure where a disposable glove may be used during the medical procedure then disposed of.

The capacitive sensor element 108 may be positioned on any suitable bendable portion of the disposable glove 100 to measure motion of any suitable part of the human hand 102. For example, the capacitive sensor element may be positioned to track motion of a lower finger joint, an upper finger joint, or a knuckle joint of any finger on the human hand. In some examples, the capacitive sensor element may be positioned on a finger tip portion of the glove.

Figure 3:
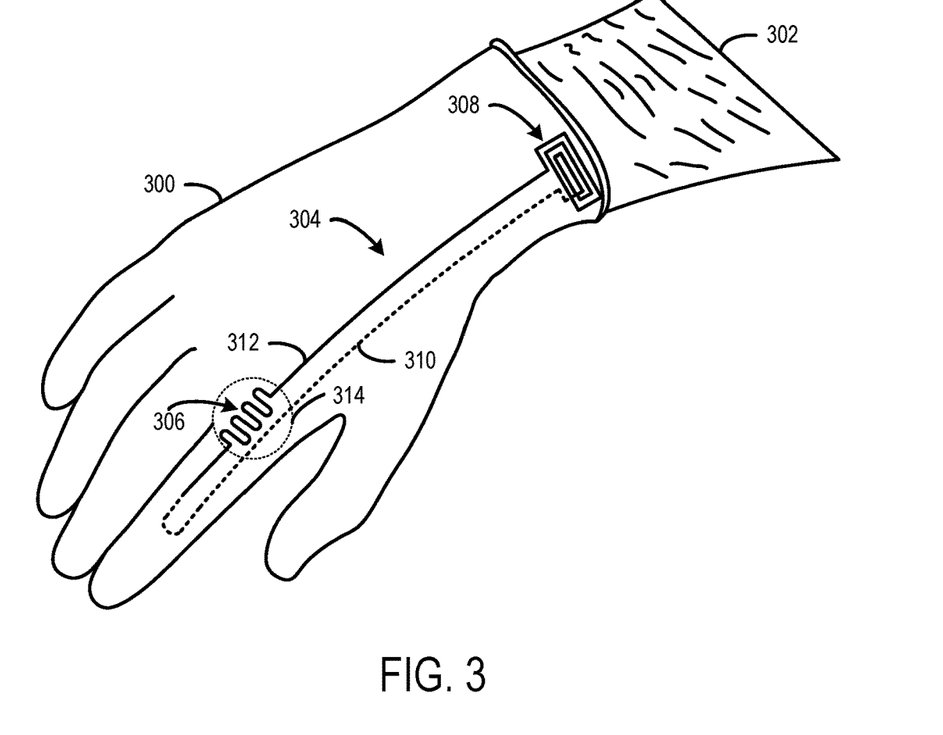
FIG. 3 schematically shows an example disposable glove comprising a sensing circuit loop including a resistive sensor element.

The capacitive sensor element is one example of a sensor element that may be included in the sensing circuit loop to measure a physical quantity. FIG. 3 shows another example implementation of a sensing-enabled, disposable glove 300 for a human hand 302 that comprises a sensing circuit loop 304 including a resistive sensor element 306 and an inductive coil 308. The pattern of the sensing circuit loop 304 forms a passive resistor-inductor (RL) circuit, where the resistive sensor element 306 functions as a sensor for measuring a physical quantity. The inductive coil 308 may enable the reusable sensor readout device 600 (shown in FIGS. 6 and 7) to inductively couple with the sensing circuit loop 304. When inductively coupled, the reusable sensor readout device may perform a frequency scan of the sensing circuit loop to measure the resistance of the resistive sensor element 306 based on the electrical behavior, and converts it into physical quantity. As an example, the reusable sensor readout device may measure the physical quantity by determining a quality (Q) factor or bandwidth of the sensing circuit loop 304 that monotonically varies according to changes in resistance.

In this implementation, the sensing circuit loop 304 may be formed in a multi-step/layer process. A first layer of conductive material (e.g., silver ink) 310 may be printed on the disposable glove 300. A dielectric layer is formed on the first layer of conductive material in appropriate locations to provide electric insulation to the second layer of conductive material. The resistive sensor element may be located on any layer of conductive material and may comprise any suitable conductive material that produces a desired range of resistance. In one example, the resistive sensor element comprises carbon. In another example, the resistive sensor element comprises silver. The resistive sensor element may be formed from a different concentration of silver ink than the other layers of the sensing circuit loop 304.

In the depicted example, the resistive sensor element 306 is positioned on a bendable finger joint portion 314 on the disposable glove 300 to align with a knuckle joint of the index finger when the disposable glove 300 is worn on the human hand 302. The resistive sensor element 306 is configured as a motion sensor that measures a change in posture/position/angle of the knuckle joint. The resistive sensor element 306 may be positioned on any suitable bendable portion of the disposable glove 300 to measure motion of any suitable part of the human hand 302. For example, the resistive sensor element may be positioned to track motion of a lower finger joint, an upper finger joint, or a knuckle joint of any finger on the human hand. In some examples, the resistive sensor element may be positioned on a finger tip portion of the disposable glove.

In some implementations, a sensor element of a sensing circuit loop may be configured to measure one or more physical quantities different than motion/posture/position/angle. For example, a sensor element of a sensing circuit loop may be configured as a chemical sensor comprising a chemically-sensitive material having an electrical property that varies in the presence of one or more selected chemical species, whether in a gaseous, liquid or solid state. As one example, a chemical sensor may include reduced graphene oxide to detect at least one of nitrogen dioxide, ammonia, and/or chlorine vapor. In another example, the chemical sensor may include a polythiophene conductive polymer (CP)-configured to detect volatile organic compounds, such as acetone, methylene chloride, toluene, and/or cyclohexane. In other examples, a chemical sensor may include various nanostructures (e.g. nanoparticles nanotubes, nanocubes, or nanosheets, depending upon the material) configured to detect different chemicals. For example, a chemical sensor may include gold, carbon nanotube/polystyrene nanocomposite (CNT/PS), or polypyrrole (PPy) to detect hydrogen peroxide. In another example, a chemical sensor may include silver, lead oxide, cobalt phthalocyanine, PPy, or CNT to detect glucose. In another example, a chemical sensor may include polybutylene (PB) to detect lactate or glutamate. In another example, a chemical sensor may include graphene to detect ascorbic acid, dopamine, or uric acid. In another example, a chemical sensor may include PEDOT:PSS to detect chlorpyrifos-oxon or bisphenol A. In another example, a chemical sensor may include multiwall carbon nanotube/polysulfone (MWCNT/PSf) to detect hCG hormone. In another example, a chemical sensor may include cobalt phthalocyanine to detect organophosphates, such as pesticides. In another example, a chemical sensor may include Au—$TiO_2$ to detect hexavalent chromium. In another example, a chemical sensor may include CNT/Cu (II) doped conductive polymer-dodecylsulfate (CP-DDS) to detect sodium alkylsufaltes. In each of these examples, the sensing material may exhibit a change in resistance in the presence of the species of interest, thereby allowing the changes in resistance to be detected as described herein.

In other examples, a sensor element of a sensing circuit loop may be configured as a temperature sensor and may include a thermally-sensitive material having an electrical property (e.g., resistance) that varies based on temperature. In further examples, a sensor element of a sensing circuit loop may be configured as an ultraviolet radiation sensor, wherein the sensor element may include ultraviolet-sensitive material having an electrical property (e.g., resistance) that varies based on exposure to ultraviolet radiation, such as titanium dioxide or zinc oxide. In yet other examples, a sensor element of a sensing circuit loop may be configured as a moisture sensor, wherein the sensor element may include moisture-sensitive material having an electrical property (e.g., capacitance) that varies based on exposure to moisture, such as hygroscopic polymer materials. It will be appreciated that a sensor element of a sensing circuit loop may be configured as any suitable sensor element configured to measure any suitable physical quantity.

Figure 4:
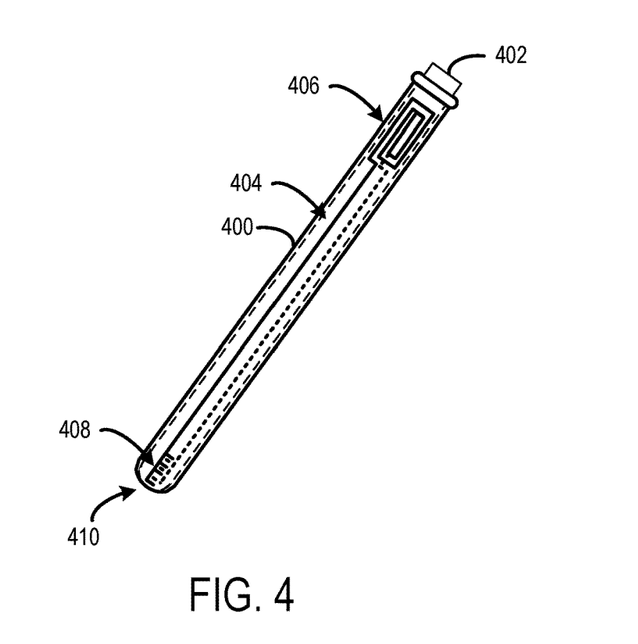
FIG. 4 schematically shows an example disposable cover for an object comprising a sensing circuit loop including a capacitive sensor element.

In some implementations, a passive sensing circuit loop may be printed on a disposable cover for an object other than a human hand. FIG. 4 shows an example disposable cover 400 for an object in the form of a medical probe 402. A sensing circuit loop 404 is printed on the disposable cover 400. The sensing circuit loop 404 includes an inductive coil 406 and a capacitive sensor element 408. The inductive coil 406 may enable an inductive coupling with a reusable sensor readout circuit that is configured to measure the capacitance of the capacitive sensor element 408, which is varying according to a physical quantity. The capacitive sensor element 408 is positioned on the disposable cover 400 to align with a tip end 410 of the medical probe 402 when the disposable cover 400 is placed on the medical probe 402. The capacitive sensor element 408 may be configured to measure any type of physical quantity that is relevant to a medical application. In one example, the capacitive sensor element 408 is configured as a temperature sensor, and the medical probe 402 may be used as a thermometer for taking the temperature of a patient. In another example, the capacitive sensor element 408 is configured to measure blood glucose levels, and the medical probe 402 may be used for a patient with diabetes. In yet other examples, a disposable cover for an object comprising a passive sensing circuit loop may be used with object other than medical probes and wearable devices, but instead with any other object in which a disposable sensing interface is desired.

Figure 5:
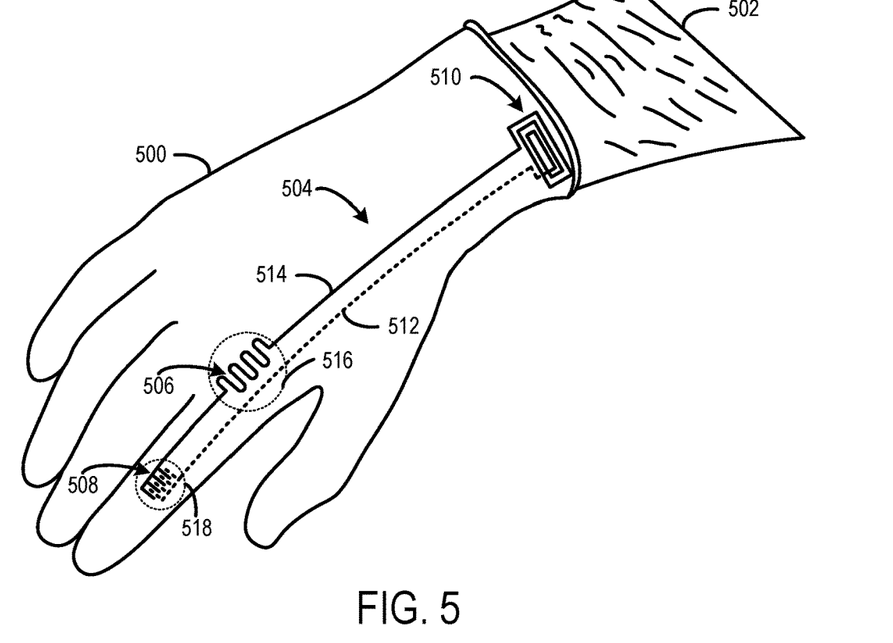
FIG. 5 schematically shows an example disposable glove comprising a sensing circuit loop including a capacitive sensor element and a resistive sensor element.

In some implementations, a sensing circuit loop printed on a disposable glove (or a disposable cover for another object) may include a plurality of sensor elements. FIG. 5 shows an example of a sensing-enabled, disposable glove 500 for a human hand 502 that comprises a sensing circuit loop 504 including a resistive sensor element 506 and a capacitive sensor element 508, in addition to an inductive coil 510. The pattern of the sensing circuit loop 504 forms a passive resistor-inductor-capacitor (RLC) circuit, where the capacitive sensor element 508 functions as a sensor for measuring a first physical quantity and the resistive sensor element 506 functions as a sensor for measuring a second, different physical quantity. In other words, the capacitive sensor element 508 converts the first physical quantity into a capacitance that can be measured and the resistive sensor element 506 converts the second physical quantity into a resistance that can be measured. The inductive coil 510 may enable the reusable sensor readout device 600 (shown in FIGS. 6 and 7) to inductively couple with the sensing circuit loop 504. When inductively coupled, the reusable sensor readout device may perform a frequency scan of the sensing circuit loop 504 to measure the capacitance of the capacitive sensor element 508 and the resistance of the resistive sensor element 506 based on the electrical behavior.

In the example of FIG. 5, both the capacitance and the resistance may be measured via a single frequency scan process. For example, the first physical quantity, based on the capacitance, may be measured by determining a resonant frequency that varies according to changes in capacitance of the capacitive sensor element 508. The second physical quantity, based on the resistance, may be measured by determining a Q-factor or bandwidth that varies according to changes in resistance of the resistive sensor element 506.

In this implementation, the sensing circuit loop 504 may be formed in a multi-step/layer process. A first layer of conductive material (e.g., silver ink) 512 may be printed on the disposable glove 500. A dielectric layer is formed on the first layer of conductive material in appropriate locations to provide electric insulation to the second layer of conductive material. For example, the inductive coil 510 may be formed in a multi-step/layer process. Likewise, the capacitive sensor element 508 and/or the resistive sensor element 506 may be printed on the disposable glove 500 in a multi-step/layer process. The sensing circuit loop may use either a mechanical via or may create a capacitor to electrically close the sensing circuit loop 504.

In the depicted example, the resistive sensor element 506 is positioned on a bendable finger joint portion on the disposable glove 500 to align with a knuckle joint of the index finger when the disposable glove 500 is worn on the human hand 502, and is configured as a motion sensor that measures a change in posture/position/angle of the knuckle joint. Likewise, the capacitive sensor element 508 is positioned on a bendable joint portion 518 of the disposable glove 500 to align with an upper finger joint of the index finger when the disposable glove 500 is worn on the human hand 502, and also is configured as a motion sensor that measures a change in posture/position/angle of the upper finger joint 518. The resistive sensor element 506 and the capacitive sensor element 508 may be positioned on any suitable bendable portions of the disposable glove 500 to measure motion of any suitable part of the human hand 502. Note that this configuration of the sensing circuit loop enables the posture/position/angle of two different portions of the human hand to be determined via a single frequency scan of the sensing circuit loop 504.

In some implementations, a plurality of sensing circuit loops each including one or more sensor elements may be printed on a disposable glove. For example, a sensing circuit loop corresponding to each finger of a human hand may be printed on a disposable glove to track motion of each of the fingers of the human hand.

Figure 6:
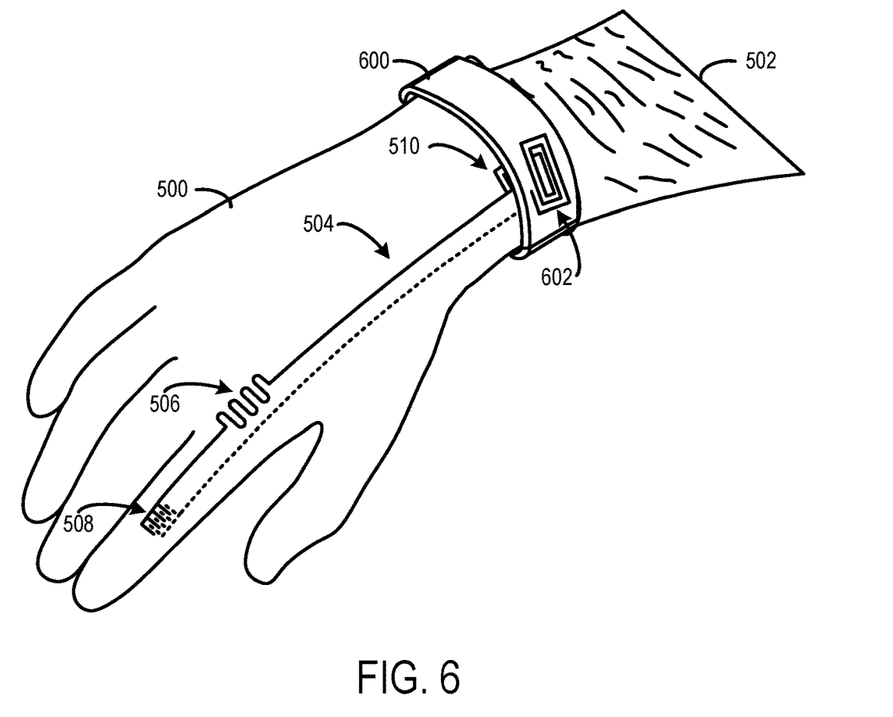
FIG. 6 schematically shows an example implementation of a sensor readout device inductively coupled to a sensing circuit loop of a disposable glove.

FIG. 6 shows an example reusable sensor readout device 600 being worn on a wrist portion of the human hand 502 such that the reusable sensor readout device 600 is aligned to inductively couple with the inductive coil 510 of the sensing circuit loop 504. In particular, the reusable sensor readout device 600 includes an inductive coil 602 that is driven with an electrical current to form the inductive coupling between the inductive coil 510 of the sensor circuit loop and the inductive coil 602 of the reusable sensor readout device. When the reusable sensor readout device 600 is inductively coupled to the sensing circuit loop 504, the reusable sensor readout device 600 performs a frequency scan to measure the capacitance of the capacitive sensor element 508 and the resistance of the resistive sensor element 506. As discussed above, the reusable sensor readout device 600 may determine a posture/position/angle of the knuckle joint from the resistance and a posture/position/angle of the upper finger joint of the index finger from the capacitance.

The reusable sensor readout device 600 may take any suitable form. In the depicted example, the reusable sensor readout device takes the form of a wrist-worn device. In another example, the reusable sensor readout device may take the form of a back-hand attachment. In yet another example, the inductive coil of the sensing circuit loop may be printed on a finger portion of the disposable glove, and the reusable sensor readout device may take the form of a ring worn on the finger. It will be appreciated that the inductive coil 510 may be printed on any suitable portion of the disposable glove 500 in order to align with the reusable sensor readout device 600.

This system architecture allows users to reuse the sensor readout device while also allowing the sensor-integrated disposable glove to be discarded after use, thereby facilitating applications with sanitary requirements.

Figure 7:
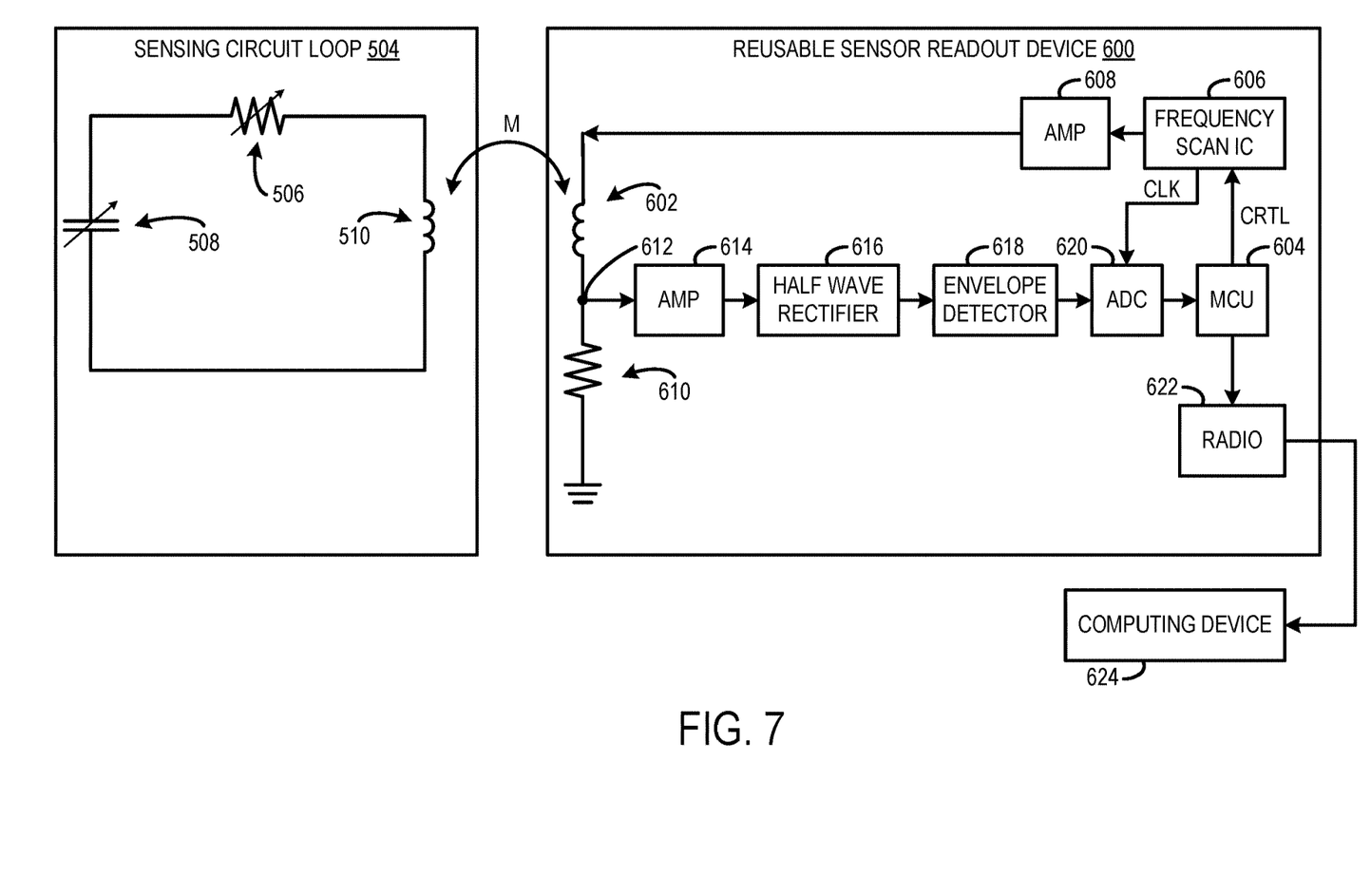
FIG. 7 schematically shows an example sensing circuit loop and sensor readout device.

FIG. 7 shows a schematic block diagram of example electronics for the reusable sensor readout device 600 and the sensing circuit loop 504. The reusable sensor readout device includes a microcontroller unit (MCU) 604 configured to control a frequency scan integrated circuit (IC) 606 based on a control signal (CRTL). The frequency scan IC 606 is configured to output a waveform that varies in frequency over a designated frequency range (e.g., 1-25 MHz). The output waveform generated by the frequency scan IC 606 is amplified by an operational amplifier or other suitable amplifier (AMP) 608 to amplify the electrical current of the output waveform. The amplified signal is provided from the operational amplifier 608 to drive the inductive coil 602. When the inductive coil 602 is driven with the electrical current, an inductive coupling is formed with the inductive coil 510 of the sensing circuit loop 504. While the two inductive coils are inductively coupled, changes in electrical behavior of the resistive sensor element 506 (e.g., Q-factor) and/or changes in electrical behavior of the capacitive sensor element 508 (e.g., resonant frequency) can be wirelessly observed in the form of a voltage response at a node of interest 612 in the reusable sensor readout device 600. In other words, the resistor 610 and the inductive coil 602 create an impedance divider that provides the voltage response representing the electrical behavior of the sensor elements of the sensing circuit loop 504.

The sensor signal observed at the node of interest 612 is amplified by an amplifier 614. The amplified signal is provided to a half wave rectifier 616 to filter out a negative component of the amplified signal. The amplified, filtered signal is provided from the half wave rectifier 616 to an envelope detector 618. The envelope detector 618 determines a magnitude envelope of the signal and outputs the magnitude envelope to an analog-to-digital converter (ADC) 620. The ADC 620 samples the signal in accordance with a clock signal (CLK) from the frequency scan IC 606 such that the ADC 620 can generate a sensor data sample for each different frequency of the frequency scan. The sensor data sample is output from the ADC 620 to the MCU 604. The MCU 604 may perform various additional signal processing operations on the received sensor data. For example, the MCU 604 may find a minimum or maximum of a frequency scan to determine a resonant frequency and measure an associated physical quantity based on the resonant frequency. In another example, the MCU 604 may determine the Q-factor and measure and associated physical quantity based on the Q-factor.

In some examples, the MCU 604 may be configured to report the sensor data to a remote computing device 624. For example, the MCU 604 may report the sensor data in real-time using a dedicated radio communication channel 622, such as Bluetooth or Wi-Fi. Such operation may allow the reusable sensor readout device 600 to provide an untethered user experience. The computing device 624 may store the sensor data and/or provide additional processing of the sensor data.

Figure 8:
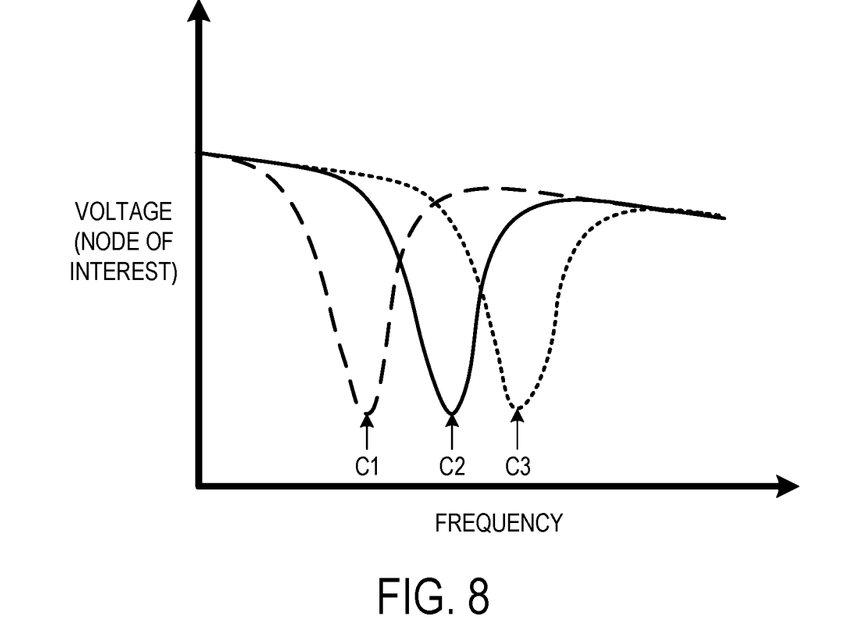
FIG. 8 is a graph illustrating a dependence of a resonant frequency on a capacitive sensor element of an example sensing circuit loop.

FIG. 8 is a graph illustrating a dependence of a resonant frequency as a function of electrical behavior of a capacitive sensor element of a sensing circuit loop. The graph shows three different signals from three different frequency scans that are performed with three different capacitances (e.g., C1, C2, C3) of the capacitive sensor element. For each frequency scan, the voltage of the signal varies across a frequency range of the frequency scan with the lowest voltage representing the resonant frequency for the frequency scan. In the depicted example, the resonant frequency varies from scan to scan as the capacitance of the capacitive sensor element varies. The resonant frequencies within the range of frequencies in the frequency scan may be mapped to any suitable physical quantity that varies with changes in capacitance of the capacitive sensor element. For example, changes in resonant frequency may correspond to changes in position of a finger joint that is aligned with the capacitive sensor element.

Figure 9:
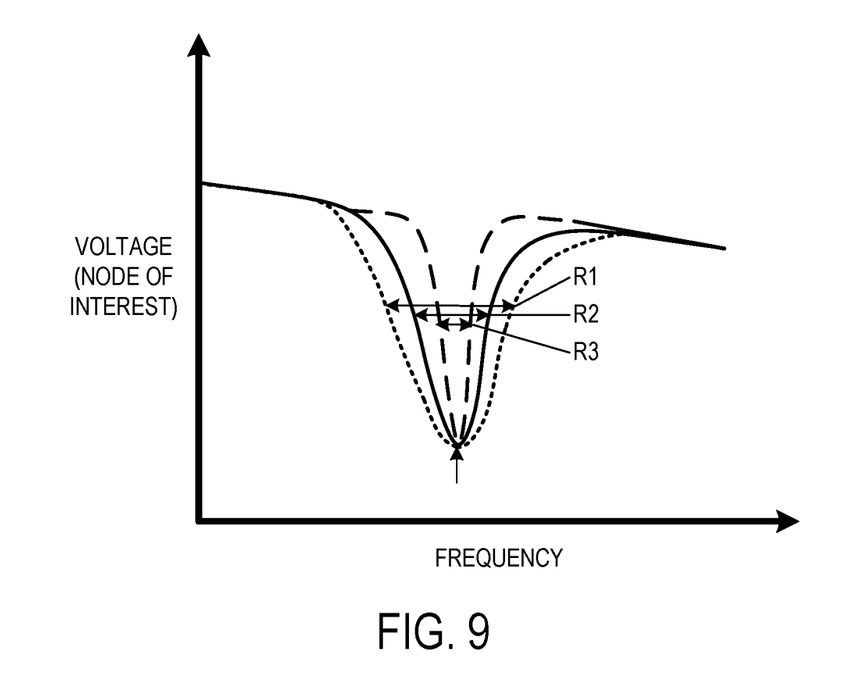
FIG. 9 is a graph illustrating a dependence of a bandwidth or quality factor on a resistive sensor element of an example sensing circuit loop.

FIG. 9 is a graph showing that a bandwidth or Q-factor of a resonant frequency varies based on electrical behavior of a resistive sensor element of a sensing circuit loop. The graph shows three different signals from three different frequency scans that are performed with three different resistances (e.g., R1, R2, R3) of the resistive sensor element. For each frequency scan, the voltage of the signal varies across a frequency range of the frequency scan with the lowest voltage representing the resonant frequency for the frequency scan. In the depicted example, the resonant frequency does not vary from scan to scan, however, the Q-factor or bandwidth of the valley created by resonant frequency varies as the resistance of the resistive sensor element varies. The range of different Q-factors may be mapped to any suitable physical quantity such that the physical quantity can be measured based on the Q-factor that varies with changes in resistance of the resistive sensor element. For example, changes in the Q-factor may correspond to changes in position of a finger joint that is aligned with the resistive sensor element.

Figure 10:
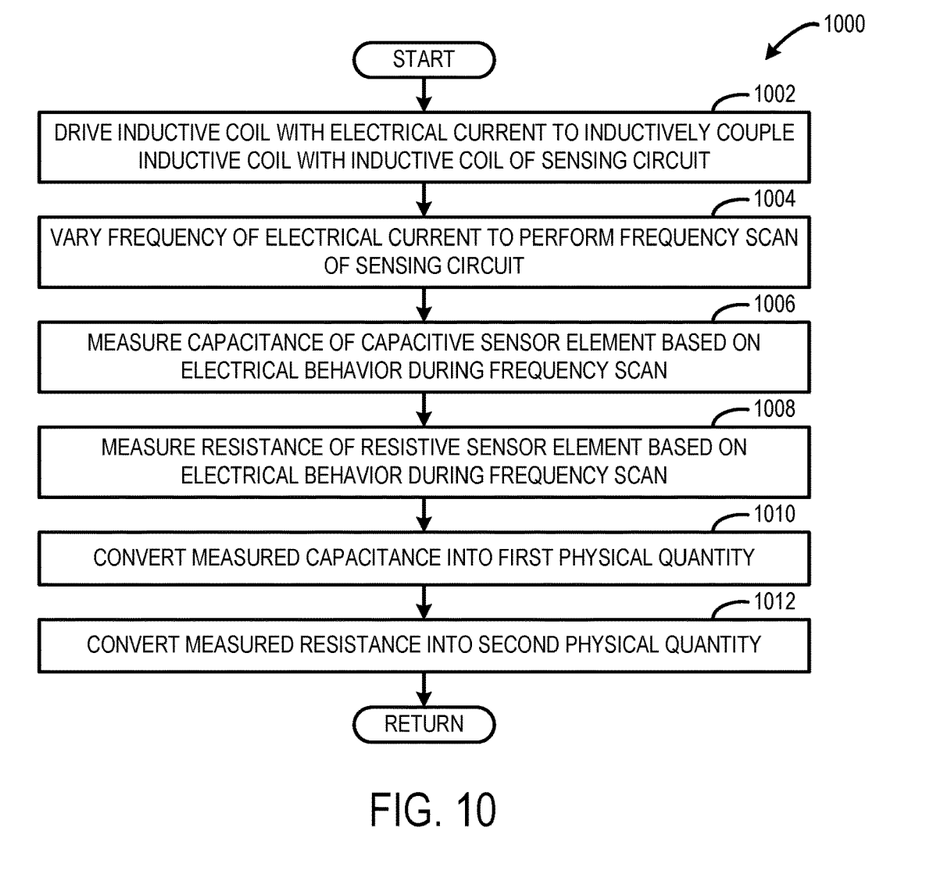
FIG. 10 shows an example method for measuring multiple different physical quantities from a single frequency scan of an inductive sensing circuit loop including multiple sensor elements.

FIG. 10 shows an example method 1000 for measuring different physical quantities from a single frequency scan of an inductive sensing circuit loop including a plurality of sensor elements. The method may be performed by the reusable sensor readout device 600 of FIGS. 6 and 7 to measure sensor data from the sensing circuit loop 504 printed on the disposable glove 500 of FIGS. 5 and 6. More generally, the method may be performed by any suitable sensor readout device to measure sensor data from multiple sensor elements in a sensing circuit loop. At 1002, the method 1000 includes driving an inductive coil of the reusable sensor readout circuit with an electrical current to inductively couple the inductive coil of the reusable sensor readout circuit with an inductive coil of a sensing circuit loop printed on a disposable glove (or disposable cover for another object). At 1004, the method 1000 includes varying a frequency of the electrical current to perform a frequency scan of the sensing circuit loop. At 1006, the method 1000 includes measuring capacitance of a capacitive sensor element based on electrical behavior during the frequency scan. In one example, the capacitance is derived from a resonant frequency determined from the frequency scan. At 1008, the method 1000 further includes measuring resistance of the resistive sensor element based on electrical behavior during the frequency scan. In one example, the resistance is derived from a quality factor at the resonant frequency. At 1010, the method 1000 includes converting the measured capacitance into a first physical quantity. At 1012, the method 1000 includes converting the measured resistance into a second physical quantity.

In other examples, the method may include measuring capacitance of a capacitive sensor element or resistance of a resistive sensor element and converting the capacitance or the resistance into a corresponding physical quantity.

In some implementations, the methods and processes described herein may be tied to a computing system of one or more computing devices. In particular, such methods and processes may be implemented as a computer-application program or service, an application-programming interface (API), a library, and/or other computer-program product.

Figure 11:
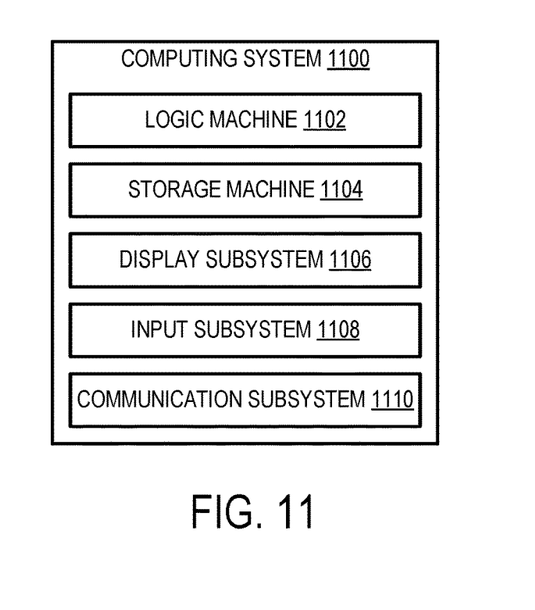
FIG. 11 schematically shows an example computing system.

FIG. 11 schematically shows a non-limiting embodiment of a computing system 1100 that can enact one or more of the methods and processes described above. Computing system 1100 is shown in simplified form. Computing system 1100 may take the form of one or more personal computers, server computers, tablet computers, home-entertainment computers, network computing devices, gaming devices, mobile computing devices, mobile communication devices (e.g., smart phone), wrist-worn devices, and/or other computing devices. For example, computing system 1100 may take the form of reusable sensor readout device 600 of FIGS. 6 and 7.

Computing system 1100 includes a logic machine 1102 and a storage machine 1104. Computing system 1100 may optionally include a display subsystem 1106, input subsystem 1108, communication subsystem 1110, and/or other components not shown in FIG. 11.

Logic machine 1102 includes one or more physical devices configured to execute instructions. For example, the logic machine 1102 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine 1102 may include one or more processors configured to execute software instructions. Additionally or alternatively, the logic machine 1102 may include one or more hardware or firmware logic machines configured to execute hardware or firmware instructions. Processors of the logic machine 1102 may be single-core or multi-core, and the instructions executed thereon may be configured for sequential, parallel, and/or distributed processing. Individual components of the logic machine 1102 optionally may be distributed among two or more separate devices, which may be remotely located and/or configured for coordinated processing. Aspects of the logic machine 1102 may be virtualized and executed by remotely accessible, networked computing devices configured in a cloud-computing configuration.

Storage machine 1104 includes one or more physical devices configured to hold instructions executable by the logic machine 1102 to implement the methods and processes described herein. When such methods and processes are implemented, the state of storage machine 1104 may be transformed—e.g., to hold different data.

Storage machine 1104 may include removable and/or built-in devices. Storage machine 1104 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 1104 may include volatile, nonvolatile, dynamic, static, read/write, read-only, random-access, sequential-access, location-addressable, file-addressable, and/or content-addressable devices.

It will be appreciated that storage machine 1104 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 1102 and storage machine 1104 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 1106 may be used to present a visual representation of data held by storage machine 1104. This visual representation may take the form of a graphical user interface (GUI). As the herein described methods and processes change the data held by the storage machine, and thus transform the state of the storage machine, the state of display subsystem 1106 may likewise be transformed to visually represent changes in the underlying data. Display subsystem 1106 may include one or more display devices utilizing virtually any type of technology. Such display devices may be combined with logic machine 1102 and/or storage machine 1104 in a shared enclosure, or such display devices may be peripheral display devices.

When included, input subsystem 1108 may comprise or interface with one or more user-input devices such as a keyboard, mouse, touch screen, or game controller. In some implementations, the input subsystem 1108 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1110 may be configured to communicatively couple computing system 1100 with one or more other computing devices. Communication subsystem 1110 may include wired and/or wireless communication devices compatible with one or more different communication protocols. As non-limiting examples, the communication subsystem 1110 may be configured for communication via a wireless telephone network, or a wired or wireless local- or wide-area network. In some implementations, the communication subsystem 1110 may allow computing system 1100 to send and/or receive messages to and/or from other devices via a network such as the Internet.

In another example, a disposable glove for a human hand comprises a sensing circuit loop printed on the disposable glove. The sensing circuit loop includes a motion sensor element printed on a bendable portion of the disposable glove, and an inductive coil printed on a different portion of the disposable glove. In this example and/or other examples, the motion sensor element may include a capacitive sensor element. In this example and/or other examples, the motion sensor element may include a resistive sensor element. In this example and/or other examples, the bendable portion may be a finger joint portion and the different portion may be a wrist portion. In this example and/or other examples, the motion sensor element may be a first motion sensor element printed on a first bendable portion of the disposable glove, and the sensing circuit loop may include a second motion sensor element printed on a second bendable portion of the disposable glove. In this example and/or other examples, the first bendable portion may be a first finger joint on a finger and the second bendable portion may be a second finger joint on the same finger. In this example and/or other examples, the first motion sensor element may comprise a capacitive sensor element and the second motion sensor element may comprise a resistive sensor element. In this example and/or other examples, the sensing circuit loop may comprise silver ink. In this example and/or other examples, the sensing circuit loop may comprise a curable resin. In this example and/or other examples, the sensing circuit loop may comprise a laminated film. In this example and/or other examples, the sensing circuit loop may comprise a plurality of separate, overlapping layers of conductive material.

In another example, a disposable cover for an object comprises a sensing circuit loop printed on the disposable cover. The sensing circuit loop includes an inductive coil, and one or more of a capacitive sensor element and a resistive sensor element. In this example and/or other examples, the capacitive or resistive sensor element may be configured as at least one of a motion sensor, a temperature sensor, an ultraviolet radiation sensor, and a moisture sensor. In this example and/or other examples, the capacitive or resistive sensor element may comprise a resistive sensor element comprising chemically-sensitive material having an electrical property that varies in the presence of one or more selected chemical species. In this example and/or other examples, the electrical property of the chemically-sensitive material may vary in the presence of one or more selected gases. In this example and/or other examples, the one or more of the capacitive sensor element and the resistive sensor element may comprise a resistive sensor element, and the sensing circuit loop may further comprise a capacitive sensor element.

In another example, a sensor readout device comprises an inductive coil, and a controller configured to drive the inductive coil with an electrical current to inductively couple the inductive coil with an inductive coil of a sensing circuit, vary a frequency of the electrical current to perform a frequency scan of the sensing circuit, measure capacitance of a capacitive sensor element based on electrical behavior during the frequency scan, measure resistance of a resistive sensor element based on electrical behavior during the frequency scan, convert the measured capacitance into a corresponding first physical quantity, and convert the measured resistance into a corresponding second physical quantity. In this example and/or other examples, the capacitance of the capacitive sensor element may be derived from a resonant frequency determined from the frequency scan. In this example and/or other examples, the resistance of the resistive sensor element may be derived from a quality factor of the resonant frequency. In this example and/or other examples, the sensor readout device may be a wrist-worn device, the sensing circuit may be printed on a disposable glove, and the sensor readout device may be configured to wirelessly provide electrical power to the sensing circuit through an inductive coupling of the inductive coil of the sensing circuit and the inductive coil of the sensor readout device.

It will be understood that the configurations and/or approaches described herein are exemplary in nature, and that these specific implementations or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A disposable glove for a human hand, comprising:
   a sensing circuit loop printed on the disposable glove, the sensing circuit loop including
      a motion sensor element printed on a finger joint portion of the disposable glove, and
      an inductive coil printed on a wrist portion of the disposable glove.

2. The disposable glove of claim 1, wherein the motion sensor element includes a capacitive sensor element.

3. The disposable glove of claim 1, wherein the motion sensor element includes a resistive sensor element.

4. The disposable glove of claim 1, wherein the motion sensor element is a first motion sensor element, wherein the finger joint portion is a first bendable portion of the disposable glove, and wherein the sensing circuit loop includes a second motion sensor element printed on a second bendable portion of the disposable glove.

5. The disposable glove of claim 4, wherein the finger joint portion is a first finger joint on a finger and the second bendable portion is a second finger joint on the same finger.

6. The disposable glove of claim 4, wherein the first motion sensor element comprises a capacitive sensor element and the second motion sensor element comprises a resistive sensor element.

7. The disposable glove of claim 1, wherein the sensing circuit loop comprises silver ink.

8. The disposable glove of claim 1, wherein the sensing circuit loop comprises a curable resin.

9. The disposable glove of claim 1, wherein the sensing circuit loop comprises a laminated film.

10. The disposable glove of claim 1, wherein the sensing circuit loop comprises a plurality of separate, overlapping layers of conductive material.

11. A disposable glove for a human hand, comprising:
a sensing circuit loop printed on the disposable glove, the sensing circuit loop including
an inductive coil printed on a wrist portion of the disposable glove, and
one or more of a capacitive sensor element and a resistive sensor element printed on a finger joint portion of the disposable glove.

12. The disposable glove of claim 11, wherein the capacitive or resistive sensor element is configured as at least one of a motion sensor, a temperature sensor, an ultraviolet radiation sensor, and a moisture sensor.

13. The disposable glove of claim 11, wherein the capacitive or resistive sensor element comprises a resistive sensor element comprising chemically-sensitive material having an electrical property that varies in the presence of one or more selected chemical species.

14. The disposable glove of claim 13, wherein the electrical property of the chemically-sensitive material varies in the presence of one or more selected gases.

15. The disposable glove of claim 11, wherein the one or more of the capacitive sensor element and the resistive sensor element comprises a resistive sensor element, and wherein the sensing circuit loop further comprises a capacitive sensor element.

16. A sensor readout device, comprising:
an inductive coil; and
a controller configured to:
drive the inductive coil with an electrical current to inductively couple the inductive coil with an inductive coil of a sensing circuit,
vary a frequency of the electrical current to perform a frequency scan of the sensing circuit,
measure capacitance of a capacitive sensor element based on electrical behavior during the frequency scan,
measure resistance of a resistive sensor element based on electrical behavior during the frequency scan,
convert the measured capacitance into a corresponding first physical quantity, and
convert the measured resistance into a corresponding second physical quantity.

17. The sensor readout device of claim 16, wherein the capacitance of the capacitive sensor element is derived from a resonant frequency determined from the frequency scan.

18. The sensor readout device of claim 17, wherein the resistance of a resistive sensor element is derived from a quality factor of the resonant frequency.

19. The sensor readout device of claim 16, wherein the sensor readout device is a wrist-worn device, wherein the sensing circuit is printed on a disposable glove, and wherein the sensor readout device is configured to wirelessly provide electrical power to the sensing circuit through an inductive coupling of the inductive coil of the sensing circuit and the inductive coil of the sensor readout device.

* * * * *